United States Patent [19]

Anderson

[11] Patent Number: 4,747,919
[45] Date of Patent: May 31, 1988

[54] APPARATUS AND METHOD FOR ELECTROPHORESIS IN TUBES

[75] Inventor: Norman L. Anderson, Washington, D.C.

[73] Assignee: Large Scale Biology Corporation, Rockville, Md.

[21] Appl. No.: 4,041

[22] Filed: Jan. 16, 1987

[51] Int. Cl.[4] ..................... G01N 27/28; G01N 27/26
[52] U.S. Cl. .............................. 204/182.8; 204/299 R
[58] Field of Search ............. 204/182.8, 182.9, 299 R

[56] References Cited

U.S. PATENT DOCUMENTS

| | | | |
|---|---|---|---|
| 2,843,540 | 7/1958 | Ressler | 204/182.8 |
| 3,867,271 | 2/1975 | Hoefer | 204/299 R X |
| 4,284,491 | 8/1981 | Vesterberg | 204/299 R |
| 4,305,799 | 12/1981 | Schwarz et al. | 204/182.9 X |

OTHER PUBLICATIONS

Ornstein, "Disc Electrophoresis-I: Background and Theory", Annals of the New York Academy of Sciences, vol. 121, pp. 321–349 (1964).
Davis, "Disc Electrophoresis-II: Method and Application to Human Serum Proteins", Annals of the New York Academy of Sciences, vol. 121, pp. 404–427 (1964).
Anderson et al, "Analytical Techniques for Cell Fractions XXI, Two-Dimensional Analysis of Serum and Tissue Proteins: Multiple Isoelectric Focusing", Analytical Biochemistry, vol. 85, pp. 331–340 (1978).

Primary Examiner—John F. Niebling
Assistant Examiner—John S. Starsiak
Attorney, Agent, or Firm—Robbins & Laramie

[57] ABSTRACT

A method and apparatus are provided for electrophoresis of macromolecules. The macromolecules are separated through a tube gel which is connected to an upper electrode buffer reservoir by means of a liquid bridge. The tubes themselves are neither permanently attached nor removably attached to the apparatus but merely rest in and abut appropriate positioning devices. Formation and maintenance of the liquid bridge is promoted by means of hydrophobic surfaces. By balancing the hydrostatic pressure of the upper chamber upon the porous or perforated surface, with the surface tension of the liquid, no leakage from the upper chamber results except by means of the stable liquid bridges.

13 Claims, 4 Drawing Sheets

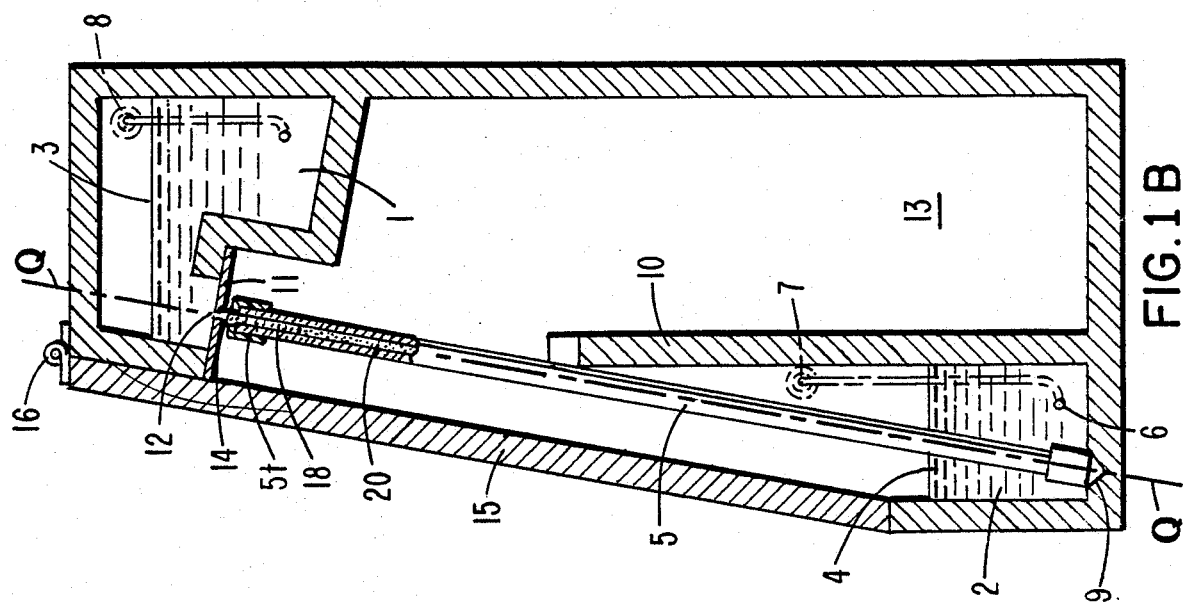
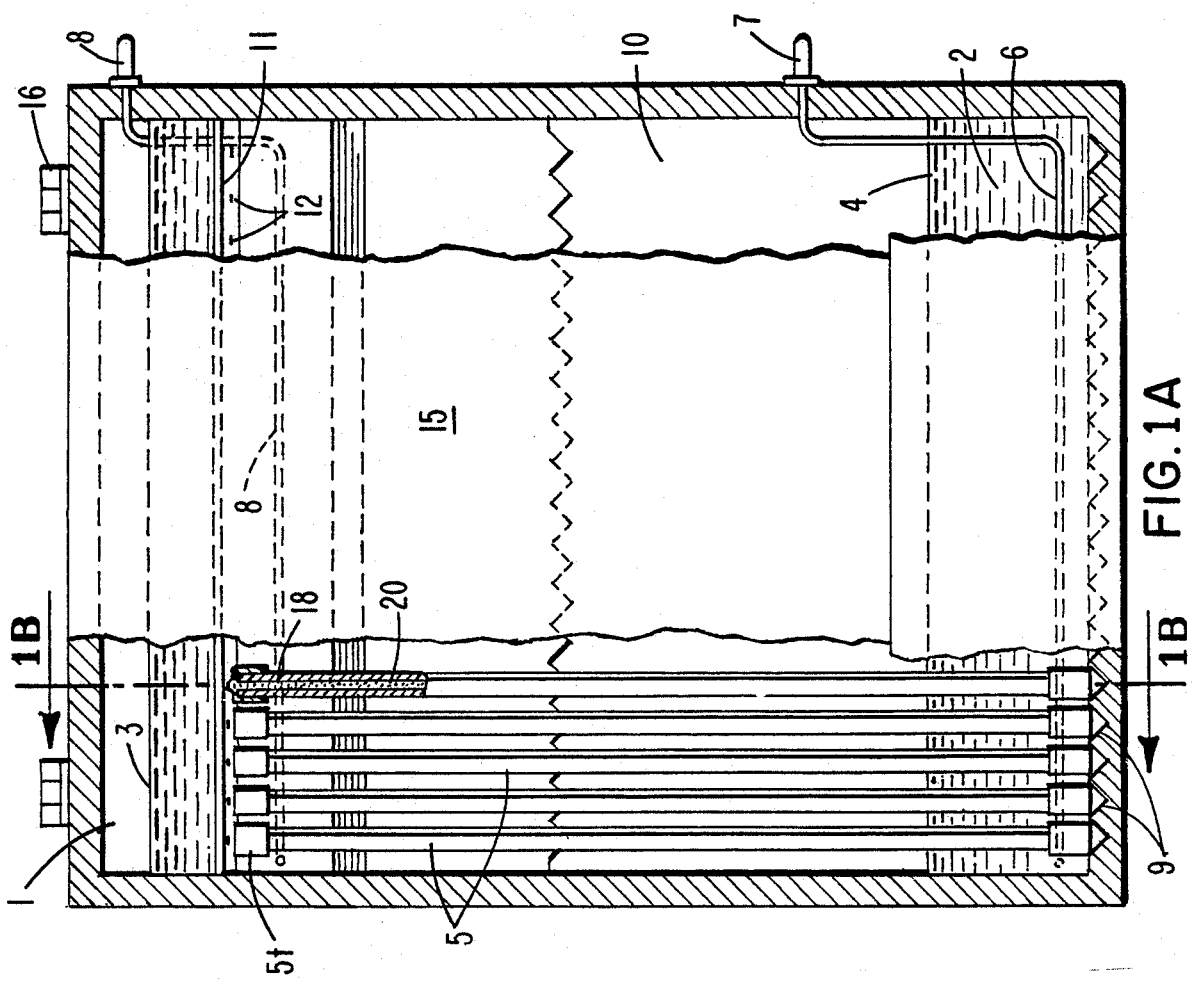

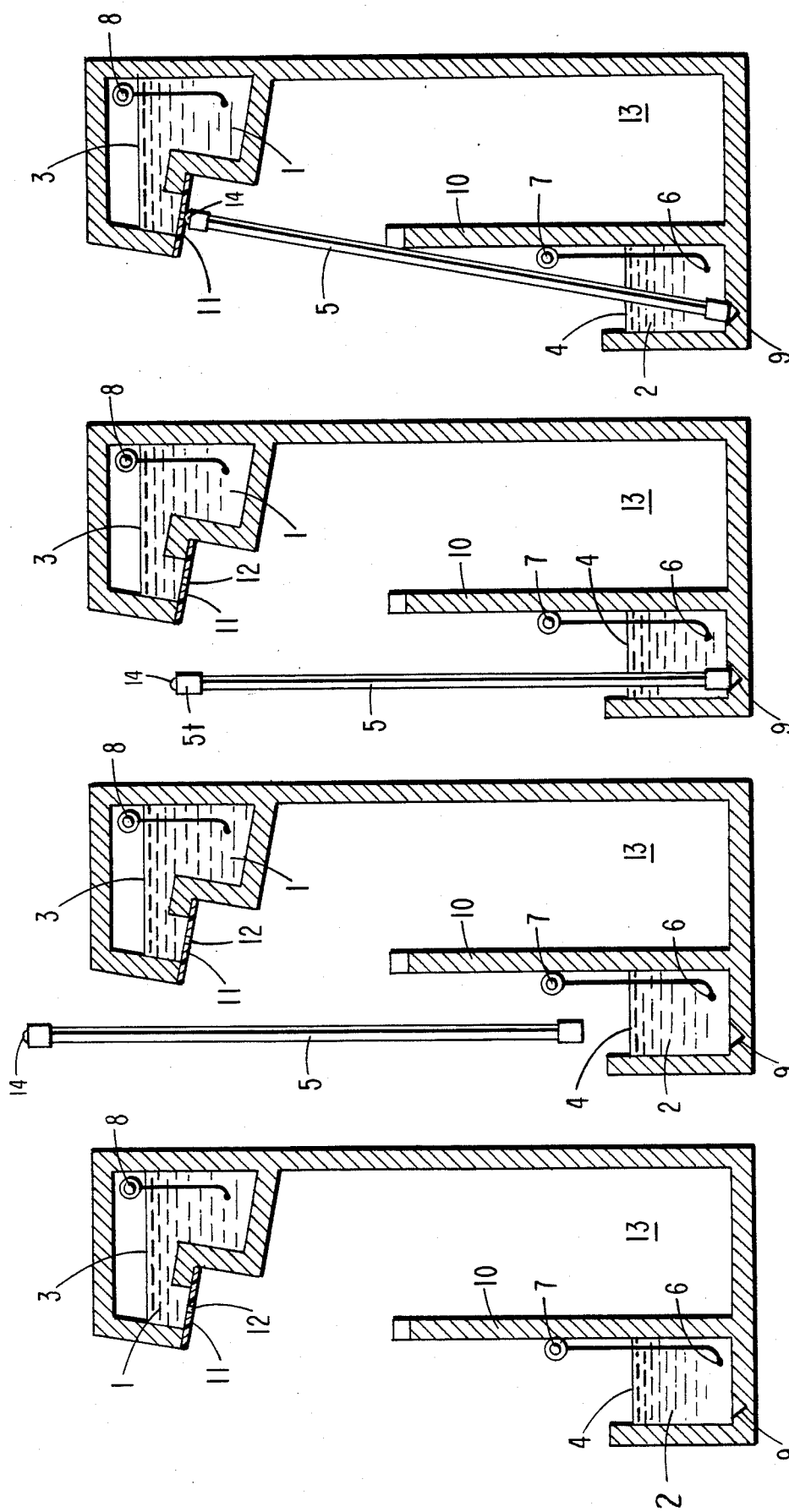

APPARATUS AND METHOD FOR ELECTROPHORESIS IN TUBES

FIELD OF THE INVENTION

The invention relates to the areas of analytical biochemistry, and clinical diagnostic techniques for detecting, quantitating, and characterizing proteins and biological samples, and for separating and characterizing nucleic acids, and for sequencing DNA.

BACKGROUND OF THE INVENTION

Generally, electrophoresis involves the migration of sample components through a medium (usually a gel) under the influence of an electric field. Electrophoresis is typically carried out in glass tubes containing rods of gel, although slab gels or paper are also used as solid supports. Electrophoresis is often used for the separation and analysis of proteins and nucleic acids. Isoelectrofocusing, a particular type of electrophoresis, is mainly used for proteins.

A typical apparatus for tube gel electrophoresis consists of a series of glass tubes mounted vertically through sealing rubber grommets into the floor of a box-like electrode-containing buffer chamber (the upper chamber). This chamber is filled with an electrode buffer once all holes in the floor are sealed with gel tubes or blanks. The lower ends of the gel tubes extend into a second buffer chamber (the lower chamber) containing a second electrode. When a voltage is applied between the upper and lower electrodes, a current flows through the tube gels.

In this type of apparatus liquid is prevented from flowing out of the upper chamber by the gel-containing tubes inserted into the tight fitting rubber grommets. An individual tube cannot be removed from the apparatus without first removing the buffer from the upper chamber. Thus, this type of apparatus is inappropriate when it is desired that individual tubes be introduced or removed at different times during electrophoresis.

Even if it is desired that all samples be run in parallel for the same duration of time, it is often not possible with these traditional systems to treat all samples identically. Loading of the gels requires a finite amount of time, therefore samples loaded first and those loaded last have not been treated identically even though the electrophoresis time might be identical. Thus, there is a need in the art for a system in which all tubes are handled individually and sequentially. There is a need for a system in which each individual sample can be handled in exactly the same way. In addition, there is a need in the art for an apparatus which is amenable to being operated automatically.

SUMMARY OF THE INVENTION

It is an object of the present invention to provide a method for gel electrophoresis of macromolecules which can be used for large or small numbers of samples.

It is another object of the present invention to provide a method of gel electrophoresis of macromolecules in tubes which can be analyzed directly or further separated by electrophoresis in another dimension.

It is yet another object of the present invention to provide an apparatus for gel electrophoresis of macromolecules in which the electrical current is conducted through a liquid bridge maintained by surface tension.

It is a further object of the present invention to provide an apparatus for gel electrophoresis of macromolecules having tubes which are freely removable.

It is still another object of the present invention to provide an apparatus for gel electrophoresis of multiple samples of macromolecules in which each sample may be electrophoresed under identical conditions serially, or under different conditions.

It is still another object of the present invention to provide an apparatus for gel electrophoresis of macromolecules in tubes in which tubes may be removed from the apparatus without disrupting the electrophoresis.

These and other objects of the invention which will be obvious to those skilled in the art are provided by one or more of the embodiments of the present invention.

According to this invention there is provided a method for electrophoresis of macromolecules through a gel medium comprising:
casting the gel medium in a vertically oriented rigid tube having a hydrophilic inner surface and a top end having a hydrophobic outer surface, the volume of said gel medium being less than the volume of the tube to form an upper gel surface below the top end of said tube;
loading the macromolecules onto the upper gel surface;
overlaying the upper gel surface with an electrode buffer to fill the tube completely and to form a convex meniscus at the top end of said tube;
placing the tube in a first reservoir containing electrode buffer such that the buffer is in direct contact with a lower gel surface;
filling a second reservoir with an electrode buffer;
establishing contact between the convex meniscus and said electrode buffer in the second reservoir to form a liquid bridge between said second reservoir and said gel medium by surface tension;
generating an electric field between the first and second reservoirs to cause the macromolecules to migrate through the gel medium.

In another embodiment of the present invention an apparatus is provided for electrophoresis of macromolecules through a gel medium comprising:
one or more rigid tubes each having a hydrophilic inner surface and a top end having a hydrophobic outer surface;
a lower chamber capable of holding liquid, wherein in a base of said chamber there are one or more dimples each capable of receiving an end of said right tubes;
an upper chamber capable of holding liquid, wherein a base of said upper chamber has apertures, the area surrounding said apertures surfaced with a hydrophobic material, said apertures each having a size and shape that prevents free flow of an aqueous liquid through said apertures and allows formation of an aqueous liquid bridge through said aperture when said aperture is contacted with an aqueous droplet from a side and a volume of liquid from an opposite side;
support means for positioning the top of said rigid tube directly under said aperture in the upper chamber.

In yet another embodiment of the present invention an apparatus is provided as described above, wherein the liquid bridge can be formed between the upper chamber and the rigid tube through a wick which comprises a porous material which remains saturated with liquid from the upper chamber and in contact with the upper reservoir, for example, by capillary action. In another embodiment an apparatus is provided wherein the liquid bridge is formed through one or more glass capillary tubes.

The present invention may be adapted for small numbers or large numbers of samples of macromolecules, each sample to be subject to electrophoresis for a particular period of time. The time may be predetermined or determined by a particular component migrating a certain distance. The system may be used for separation of proteins, nucleic acids, polysaccharides, peptides, etc. The invention may also be used in the sequencing of nucleic acids, as well as in isoelectric focusing and two dimensional gel electrophoresis.

BRIEF DESCRIPTION OF THE DRAWINGS

FIG. 1A is a front elevational view, partly in section, of the apparatus of the present invention.

FIG. 1B is a sectional view taken along line 1B—1B of FIG. 1A.

FIG. 3 shows the steps (A through D) in the positioning of a tube in the linear apparatus to form a liquid bridge.

FIG. 5 shows four embodiments of the liquid bridge between upper reservoir 1 and tube gels 5.

DETAILED DESCRIPTION OF THE INVENTION

According to the method of the present invention tube gel electrophoresis is performed wherein the electrical connection between the two electrodes is maintained through a liquid bridge. The liquid bridge is formed by means of surface tension between a reservoir containing upper electrode buffer and a convex meniscus of electrode buffer atop a tube gel. In order to prevent the convex meniscus from dissipating, i.e., the buffer escaping over the edge and running down the side of the tube, the outer surface of the top of the rigid tube is hydrophobic. The inner surface of the rigid tube is hydrophilic in character. The hydrophobic "collar" 5t prevents the liquid bridge from growing and overflowing the space between the top end of the tube and the reservoir of upper electrode buffer.

The tube itself may be made of any material which is rigid, so long as the inner surfaces of the tube are hydrophilic in nature and at least the top end of the rigid tube has an outer surface which is hydrophobic in nature to function as a collar. In general, the tube will have a uniform diameter along its length. Typically it will be a straight cylinder. However, other configurations and shapes are possible. For example, the "tube" gel can actually be in the form of a conventional slab gel. These are usually formed by enclosing a small volume between two glass plates. Often the plates are parallel. The tubes may be disposable or reusable.

The material comprising the gel 20 may be any which is ordinarily used in the art. This will vary with the particular application, but could include agarose, polyacrylamide, starch, and the like.

The hydrophobic material may be any plastic such as polystyrene, polycarbonate, polyvinylchloride, polyethylene, hydrocarbon wax, and polychlorinated or polyfluorinated plastics such as polytetrafluoroethylene. The hydrophilic inner surfaces may be made from any suitable material including glass, sapphire, quartz, and alumina, beryllia or other ceramics. The tube may be either made essentially of the hydrophilic material and coated with a hydrophobic material, or the hydrophobic material may form the tube and the inner tube surface may be coated with a hydrophilic material. An example of a suitable material for hydrophobic coating is dichlorodimethylsilane.

Figure 4:
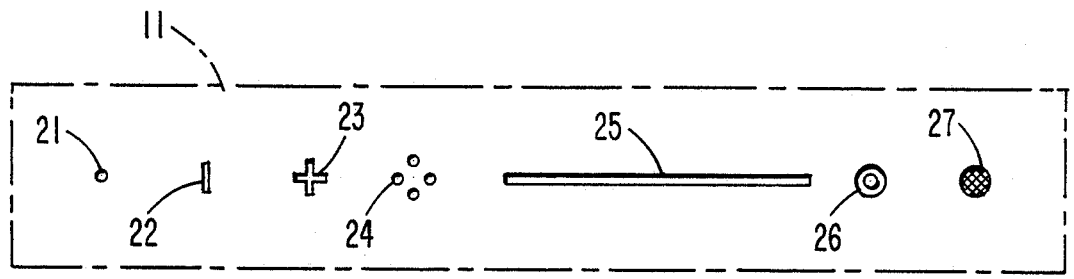
FIG. 4 shows a schematic of possible aperture configurations that might be formed in the hydrophobic floor 11 of the upper chamber. Aperture 21 is a simple pinhole; aperture 22 is a slot, typically 1 mm×0.1 mm width; aperture 23 is a cross, typically 1 mm×1 mm×0.1 mm width; aperture 24 is an array of multiple pinholes; aperture 25 is an extended slot contacting many tubes regularly spaced along it, typically 0.1 mm in width; aperture 26 is an annular slot, typically 1 mm diameter×0.1 mm width; aperture 27 is a larger hole covered with a hydrophobic mesh (e.g., teflon).
Figure 5A:
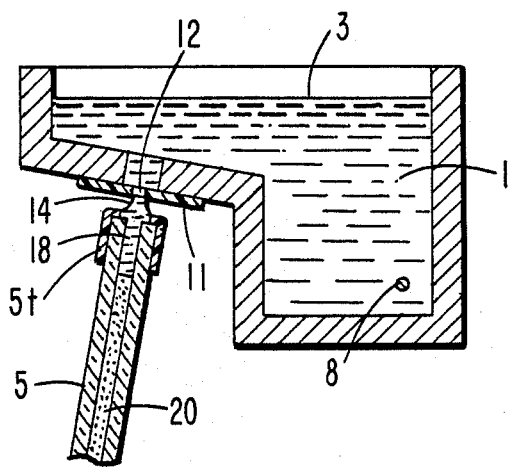
FIG. 5A shows an aperture 12 in a hydrophobic surface below the upper buffer surface.
Figure 5B:
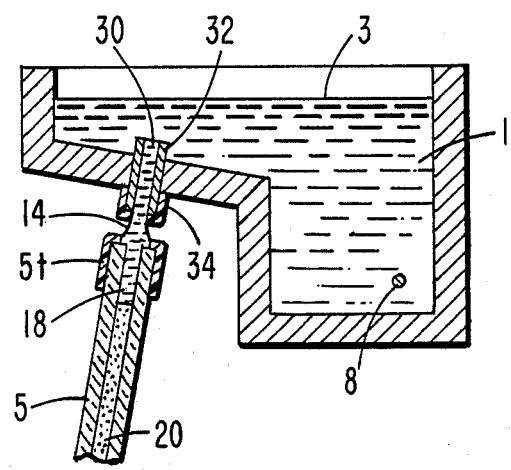
FIG. 5B shows an aperture 30 formed by a connecting capillary tube 32 with a hydrophobic collar 34, below the upper buffer surface.

The liquid bridge which is formed between the convex meniscus atop the rigid tube and the upper reservoir buffer may be formed through a small aperture in a hydrophobic material 11 on a base of the upper electrode buffer chamber. The base itself may be made of thin hydrophobic material, or the area surrounding each aperture may be surfaced with hydropobic material (see FIG. 5A). The hydrophobic material 11 containing the small apertures 12 may be flexible to allow some movement on contact with the approaching tube, thus ensuring a close contact of the hydrophobic collar and the hydrophobic lower surface of the upper reservoir. However, if the surface is rigid, precise control of the tube length and the geometry of the apparatus will desirably result in a gap between collar (upper end of tube) and hydrophobic surface in the range of 0.0 to about 1 mm. The small size and specific shape of the aperture is chosen so as to prevent the free flow of an aqueous liquid through the aperture and to allow the establishment of an aqueous liquid bridge through the aperture when an aqueous droplet approaches from the under side. For example, the aperture may be small and linear (1 mm×0.2 mm) or may be cross-shaped (1 mm×1 mm×0.2 mm), or other combinations of size and shape which function as described above (see FIG. 4). Alternatively, the aperture may be formed by a protrusion in the base, formed, for example, by a glass capillary tube 32, the opening of which is surrounded by a hydrophobic collar 34 (see FIG. 5B). It is important that the hydrostatic pressure head above the base of the chamber containing the apertures be relatively small so that the upper buffer is not forced to flow freely through the aperture.

Figure 5C:
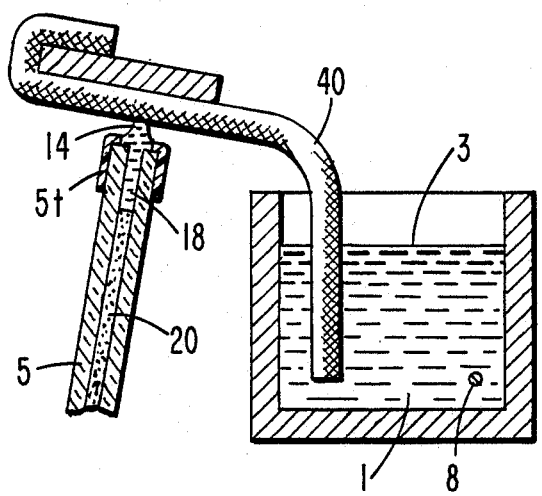
FIG. 5C shows a wick 40 extending above the upper buffer surface.
Figure 5D:
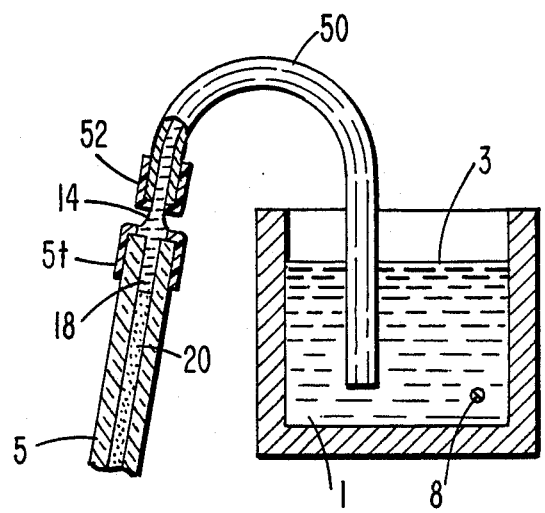
FIG. 5D shows a connecting capillary tube 50 with hydrophobic collar 52, extending above the upper buffer surface.

In yet other embodiments of the invention, the liquid bridge between the upper electrode reservoir and the gel may be formed through a wick 40 comprising a porous material such as heavy filter paper which remains saturated with upper electrode buffer and in contact with the upper reservoir, for example, by a "wicking" or capillary action (see FIG. 5C). In still another embodiment the liquid bridge may be formed through capillary tubes 50, i.e., narrow bore glass tubes, having hydrophobic outer surfaces 53 at the end through which the liquid bridge forms (see FIG. 5D). The capillary tubes 50 may draw the buffer out of the reservoir, above the level of the buffer.

Each gel tube is slightly overfilled with upper electrode buffer 18 to form a convex meniscus, or an extending droplet of fluid. It is not critical whether the gel tube is filled with electrode buffer before or after the macromolecules are loaded onto the gel surface. If loading is after, macromolecules should be in a liquid which is denser than the buffer. Because of the reliance on surface tension as a means of establishing and maintaining the liquid bridge as well as preventing flow-through of the upper electrode buffer from the upper reservoir, it is important that the upper buffer not contain a concentration of detergent or other amphiphilic component sufficient to overcome surface tension and allow free leakage of the upper buffer. The convex meniscus or extending droplet 14 which is formed atop the tube gel is prevented from dissipating and spilling over by means of the hydrophobic outer coating on the top end of the rigid tube. The hydrophobic coating may extend over the whole outer surface of the rigid tube, or it may only be at the ends of the rigid tubes, or it may be only at the top of the rigid tubes.

An apparatus is provided to perform the method of the present invention. A particular embodiment (linear) of the apparatus is shown in FIG. 1 and an alternative embodiment (circular) is shown in FIG. 2. The following description of a preferred embodiment of the apparatus will be keyed to the parts shown in FIG. 1.

Upper chamber 1 and lower chamber 2 are each filled with an appropriate amount of a suitable buffer to levels 3 and 4 respectively. Gel tubes 5 are placed so as to rest with lower ends immersed in lower chamber 2. An electrode wire or rod 6 spanning the lower chamber is connected to an externally accessible plug 7, and a similar electrode and plug 8 are provided in the upper chamber. Tubes 5 rest in conical dimples 9 in the base of the lower chamber 2, thus assuring precise positioning of the tubes and avoiding any tendency for the tubes to roll. The tubes are tilted slightly and rest on notches in support means 10. Each tube is precisely located and remains in a stable position since it is resting in a dimple and a notch.

The upper chamber 1 is formed so as to provide a shallow section with a floor of thin hydrophobic material 11. At a position immediately above where the top end of each tube is located, a small aperture 12 is formed in floor 11.

In an alternative embodiment (not shown) floor 11 is composed of a flap of porous material such as heavy filter paper a portion of which dips into the upper buffer. In the side view (FIG. 1B) an area 13 is shown which is a receptacle area for falling drops when the liquid bridge 14 is broken as a tube is removed from the apparatus. A cover plate 15 is connected to the top of upper chamber 1 by hinges 16.

The following discussion will more generally describe the apparatus of the present invention. One or more rigid tubes having a hydrophilic inner surface and a top end having a hydrophobic outer surface hold a gel material 20 in the apparatus. The hydrophobic top ends are such that they form a "collar" 5t and function to help maintain an extended droplet or convex meniscus atop a gel tube. The "collar" also serves to prevent a liquid bridge from expanding and leaking down the side of a tube. The collar also provides electrical insulation.

Suitable materials for the "collar" include plastics, such as polystyrene, polycarbonate, polyvinylchloride, polytetrafluoroethylene and the like. The inner surfaces may be any hydrophilic substances such as borosilicate, quartz, sapphire, glass, or alumina, beryllia or other ceramics. Alternatively, the hydrophilic inner surface may be formed by suitable treatment of a tube comprising hydrophobic material. Conversely, the hydrophobic outer surface may be formed by suitable treatment of a hydrophilic material. For example, a collar of heat-shrinkable teflon tubing can be used to cover the outside and partially cover the end face of a glass electrophoresis tube.

The apparatus contains a lower chamber which is capable of holding liquid and which has an electrode wire spanning the chamber and connected to an externally accessible plug. Preferably the electrode wire is equidistant from each tube end such that each tube gel is subjected to an electric field that is equivalent. The lower chamber may be shallow or deep; if deep, it can function as a temperature control device for the tubes. In the base of the lower chamber there are dimples which are capable of receiving the bottom ends of the rigid tubes. In a preferred embodiment the dimples are conical, the diameter of the base of the conical dimple, i.e., the directrix of the cone, being larger than the diameter of the tube bottom. The conical dimples serve as rests for the tubes, assuring precise positioning and avoiding any tendency for the tubes to roll or move. Other shapes for the dimples are possible. Preferably the tubes merely abut other parts of the device; they do not become attached at any point. Less preferably the tubes may be gripped or hung, being removably attached.

The conical dimples allow the tubes, after being rested into the dimples, to be slightly tilted, for example, at an angle of about 10° from vertical. In order to support the tubes, there is a support means. The support means precisely locates the tubes which rest against it. This locating may be, for example, by means of V-shaped notches. Of course other support means are possible. Once again, the tubes preferably are not attached to the support means but merely rest against or abut the support means. The support means assures that the rigid tubes remain parallel to each other and in a proper spatial orientation. The support means may alternatively be another part of the apparatus such as part of the upper or lower chamber.

The upper chamber which holds the upper electrode buffer also contains an electrode wire which spans the entire chamber and is preferably equidistant from all tubes. The electrode wire is connected to an externally accessible plug. In one embodiment, the upper chamber has a base having apertures, the area surrounding said apertures being surfaced with a hydrophobic material. The size and shape of the aperture are chosen so as to prevent the free flow of an aqueous liquid through the aperture and to allow the establishment of an aqueous liquid bridge through the aperture when an aqueous droplet approaches from the opposite side. For example, the base may consist of a thin Teflon TM (polytetrafluoroethylene) sheet with small circular, linear or cross-shaped apertures in it. Alternatively, the base may be made from another type of material with apertures in it, the area surrounding each aperture being surfaced with a hydrophobic material. The upper buffer is held in place in a stable manner when tubes are not present at one or more positions in the apparatus.

In another embodiment of the present invention the upper chamber contains a flap or surface which is composed of a porous material which can be saturated with and in contact with liquid from the upper chamber, for example, by capillary action (See FIG. 5c). A liquid bridge can be formed and maintained through this porous material between the extended droplet or convex meniscus atop the rigid tube on one side and the upper reservoir on the opposite side. If necessary, a small pump can be used to continuously wet the porous material if the capillary action is insufficient.

To form a liquid bridge and an electrical connection, a rigid tube is positioned vertically over the lower chamber in an unoccupied position (see FIGS. 3A-3D). The tube is then lowered vertically into a dimple such that its lower edge rests in a conical dimple 9. The tube may be rocked such that it encounters the notched support means 10. The angle which the located tube forms from vertical is about 10° or less. The tube may be vertical. However if the tube is tilted when the liquid bridge is formed, when the bridge is broken the upper buffer droplet can be conveniently prevented from entering the lower reservoir, as discussed below.

Electrical contact is established between the upper and lower chambers as a result of the following principles. A tube is introduced into the apparatus with an extended droplet or convex meniscus of aqueous fluid on the top end of the tube. The collar of hydrophobic material around the top end of the tube prevents the droplet from leaking down the tube. As the tube is rocked to abut against the support means, the droplet contacts a corresponding aperture and surface tension causes the liquids to fuse, creating a liquid bridge. Once again, the hydrophobic collar around the tube prevents by means of surface tension the liquid bridge from growing and overflowing the connection. In the embodiment where the tube collar closely approaches the hydrophobic under-surface of the upper chamber, thus causing the convex meniscus to form a partial droplet extending out of the region of contact, a means may be provided for removing this excess on insertion of the tube. Such means may comprise a filter paper wick or a suction tube. In the embodiment where the upper chamber contains a porous surface or flap (wick), as the rigid tube is rocked backed to contact the support means, the extended droplet contacts the saturated porous material and a liquid bridge is also formed.

When the tube is removed, the liquid bridge is broken. To prevent a droplet from the liquid bridge from falling into the lower chamber, the lower chamber can be arranged such that it is not positioned vertically below the aperture or point of contact of the tubes with the saturated porous material. A receptacle may be positioned vertically beneath the liquid bridges to catch any falling droplets.

Two particular geometric configurations are contemplated for the apparatus of the present invention. In one the rigid tubes form a linear array (see FIGS. 1A, 1B). Thus, the arrangement of the apertures describes a first line and the arrangement of the dimples in the base decribes a second line parallel to the first line. The two parallel lines describe a plane Q (See FIG. 1B). Each aperture and a corresponding dimple form the end points of a line segment which is perpendicular to the first and second lines formed by the apertures and dimples respectively. The angle formed by the intersection of the base of the lower chamber and the plane Q described by the two parallel lines is between about 80° and 90°. Thus, the arrangement of the rigid tubes is such that they are all parallel to each other, and vertical or just slightly off (less than about 10°) of vertical.

Figure 2A:
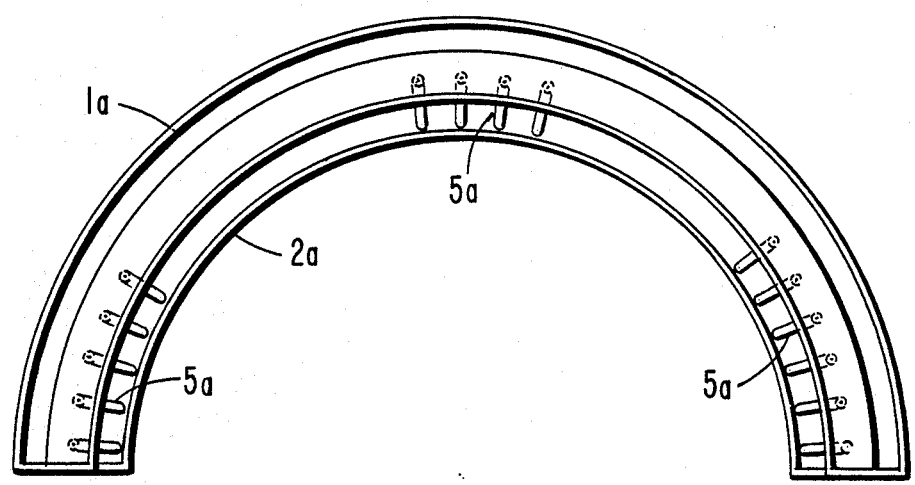
FIGS. 2A and 2B are schematic top plan and front elevation, respectively, of the apparatus arranged in the form of a circular arc; the suffix "a" was added to the reference numbers of parts like those of FIG. 1.
Figure 2B:
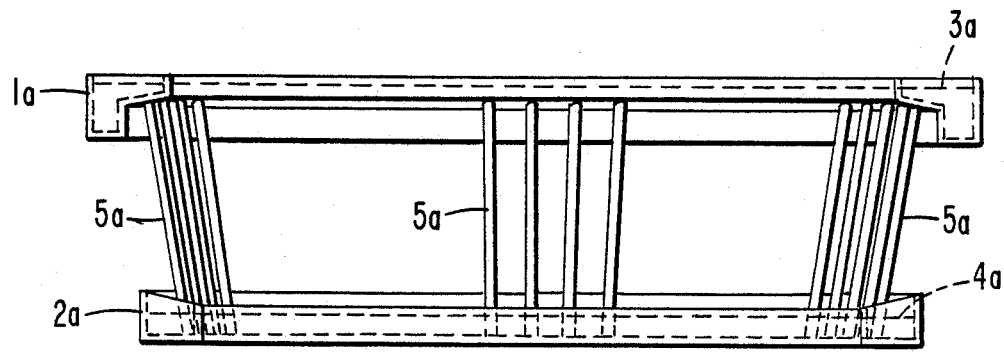

In another contemplated geometry the tubes in the apparatus form a circular configuration (see FIGS. 2A and 2B). Thus, the arrangement of the apertures and the arrangement of the dimples each describe a circle. The centers of the two circles describe a line which is perpendicular to the plane of each of said circles. The circles, being of non-equivalent sizes, lie on the surface of an imaginary right circular cone. The base of said lower chamber, i.e., the plane containing the circle of dimples, forms an angle of between about 80° and 90° with any line which passes through both the vertex and the directrix of the cone.

Even though the geometrical configurations of the apparatus have been described in terms of the embodiment containing apertures in the upper chamber, these geometries are equally useful in the embodiment which contains a porous surface as the means of forming a liquid bridge. The geometries described for the apparatus allow that access for loading or removing tubes can be either linear, circumferential with inner access, or circumferential with outside access (like a "lazy susan").

The benefits of using the apparatus of the present invention include the ease with which tubes can be introduced and removed at any time by means of a simple series of horizontal, vertical and rocking motions. In addition, the apparatus can be operated with relatively large numbers or relatively small numbers of tube gels. The use of the non-attached tube gels and the liquid bridge will facilitate the use of this method in automated, robotic systems.

Other embodiments will occur to those of skill in the art. The invention is not limited to these embodiments but is represented solely by the claims appended below.

I claim:

1. A method of electrophoresis of macromolecules through a gel medium comprising:
    casting the gel medium in a vertically oriented, rigid tube having a hydrophilic inner surface and a top end having a hydrophobic outer surface, the volume of said gel medium being less than the volume of the tube, to form an upper gel surface below the top end of said tube;
    loading the macromolecules onto the upper gel surface;
    overlaying the upper gel surface with an electrode buffer to fill the tube completely and to form convex meniscus at the top end of said tube;
    placing the tube in a first reservoir containing an electrode buffer such that the buffer is in direct contact with a lower gel surface;
    filling a second reservoir with an electrode buffer;
    establishing contact between the convex meniscus and said electrode buffer in the second reservoir to form a liquid bridge between said second reservoir and said gel medium by surface tension;
    generating an electric field between the first and second reservoirs to cause the macromolecules to migrate through the gel medium.

2. The method of claim 1 wherein the step of establishing contact to form a liquid bridge is performed by the steps of:
    providing a wick which is in contact with the electrode buffer in the second reservoir; and
    contacting said wick with said convex meniscus.

3. The method of claim 1 wherein the step of establishing contact to form a liquid bridge is performed by the steps of:
prov234ing that said second reservoir has one or more apertures in a base, the area of the base surrounding said apertures surfaced with a hydrophobic material, said apertures having a size and shape that prevent free flow of aqueous liquid through said apertures; and
contacting the convex meniscus with said apertures.

4. The method of claim 1 wherein the step of establishing contact to form a liquid bridge is performed by the steps of:
providing one or more capillary tubes, a first end of said capillary tubes being immersed in said electrode buffer in the second reservoir, and a second end of said capillary tubes being surfaced with a hydrophobic material, said second end extending out of said electrode buffer; and
contacting said second end of said capillary tube with the convex meniscus.

5. The method of claim 1 wherein the hydrophilic inner surfaces of the rigid tubes comprise material selected from the group consisting of glass, sapphire, quartz, alumina and beryllia.

6. The method of claim 1 wherein the hydrophobic outer surfaces of said rigid tubes comprise a material selected from the group consisting of polystyrene, polycarbonate, polyvinyl chloride, polyethylene, hydrocarbon wax, polychlorinated plastics and polyfluorinated plastics.

7. An apparatus for electrophoresis of macromolecules through a gel medium comprising:
one or more rigid tubes each having a hydrophilic inner surface and a top end having a hydrophobic outer surface;
a lower chamber capable of holding liquid, wherein in a base of said chamber there are one or more dimples each capable of receiving an end of said rigid tube;
an upper chamber capable of holding liquid, wherein a base of said upper chamber has one or more apertures, the area surrounding said apertures surfaced with a hydrophobic material, said apertures having a size and shape that prevent free flow of an aqueous liquid through said apertures and allows formation of an aqueous liquid bridge through said apertures when said apertures are contacted with an aqueous droplet from a side and a volume of liquid from an opposite side;
support means for positioning the top of said rigid tube directly under said aperture in the upper chamber.

8. The apparatus of claim 7 wherein the hydrophilic inner surfaces of said rigid tubes comprise a material selected from the group consisting of glass, sapphire, quartz, alumina and beryllia..

9. The apparatus of claim 7 wherein the hydrophobic outer surfaces of said rigid tubes comprise a material selected from the group consisting of polystyrene, polycarbonate, polyvinyl chloride, polyethylene, hydrocarbon wax, polychlorinated plastics, and polyfluorinated plastics.

10. The apparatus of claim 7 wherein the arrangement of said apertures describes a first line, and the arrangement of said dimples describes a second line parallel to the first line, the two lines describing a plane, each aperture and a corresponding dimple forming the end points of a line segment, said line segment being perpendicular to said first and second lines, the angle formed by the intersection of the base of the lower chamber and the plane being between about 80° and 90°.

11. The apparatus of claim 7 wherein the arrangement of said apertures and the arrangement of said dimples each describe a circle, the centers of said circles describe a line perpendicular to the plane of each of said circles, the circles lying on the surface of an imaginary right circular cone, the base of said lower chamber forming an angle between about 80° and 90° with any line which passes through both the vertex of the cone and the directrix of the cone.

12. An apparatus for electrophoresis of macromolecules through a gel medium comprising:
one or more rigid tubes each having a hydrophilic inner surface and a top end having a hydrophobic outer surface;
a lower chamber capable of holding liquid wherein in a base of said chamber there are one or more dimples for receiving a rigid tube;
an upper chamber capable of holding liquid, said upper chamber having a wick which comprises a porous material which can be saturated with and in contact with a volume of liquid in said upper chamber;
support means for positioning each of the rigid tubes parallel to one another, and proximal to said wick such that a liquid bridge can form and be maintained between said rigid tube and said volume of liquid in said upper chamber.

13. An apparatus for electrophoresis of macromolecules through a gel medium comprising:
one or more rigid tubes each having a hydrophilic inner surface and a top end having a hydrophobic outer surface;
a lower chamber capable of holding liquid wherein a base of said chamber there are one or more dimples for receiving a rigid tube;
an upper chamber capable of holding liquid, said upper chamber containing one or more capillary tubes the first end of said capillary tubes being within the upper chamber, and a second end of said capillary tubes being surfaced with a hydrophobic material, said second end extending out of said upper chamber; and
support means for positioning each of the rigid tubes parallel to one another, and proximal to said second end of said capillary tubes such that a liquid bridge can form and be maintained between said rigid tube and said liquid in said upper chamber through said capillary tubes.

* * * * *